(12) United States Patent
Chang et al.

(10) Patent No.: US 10,376,280 B2
(45) Date of Patent: Aug. 13, 2019

(54) INVERTED BOWL SHAPED ULTRASOUND PROBE STRUCTURE OF GUIDING THE PUNCTURE NEEDLE

(71) Applicants: National Yang-Ming University, Taipei (TW); National Health Research Institutes, Miaoli County (TW)

(72) Inventors: Yin Chang, Taipei (TW); Ching-Hsin Chen, Miaoli County (TW)

(73) Assignees: National Health Research Institutes, Miaoli County (TW); National Yang-Ming University, Taipei (TW)

( * ) Notice: Subject to any disclaimer, the term of this patent is extended or adjusted under 35 U.S.C. 154(b) by 3 days.

(21) Appl. No.: 14/197,942

(22) Filed: Mar. 5, 2014

(65) Prior Publication Data

US 2014/0257110 A1  Sep. 11, 2014

(30) Foreign Application Priority Data

Mar. 7, 2013  (TW) .............................. 102108012 A

(51) Int. Cl.
*A61B 8/00* (2006.01)
*A61B 8/08* (2006.01)
*A61B 17/34* (2006.01)

(52) U.S. Cl.
CPC ........ *A61B 17/3403* (2013.01); *A61B 8/0841* (2013.01); *A61B 8/4444* (2013.01); *A61B 8/4494* (2013.01); *A61B 8/4488* (2013.01); *A61B 2017/3413* (2013.01)

(58) Field of Classification Search
CPC .............. A61B 8/00; A61B 8/08; A61B 17/34
See application file for complete search history.

(56) References Cited

U.S. PATENT DOCUMENTS

| | | | | |
|---|---|---|---|---|
| 4,475,553 A | * | 10/1984 | Yamaguchi | A61B 8/0833 600/461 |
| 6,299,580 B1 | * | 10/2001 | Asafusa | B06B 1/0637 600/459 |
| 6,613,005 B1 | * | 9/2003 | Friedman | A61N 7/02 600/371 |
| 6,666,835 B2 | * | 12/2003 | Martin | A61B 17/22004 601/2 |
| 2001/0020131 A1 | * | 9/2001 | Kawagishi | G10K 11/346 600/443 |
| 2008/0275370 A1 | * | 11/2008 | McIntyre | A61F 9/00745 601/2 |
| 2009/0105597 A1 | * | 4/2009 | Abraham | A61B 8/08 600/466 |
| 2010/0168583 A1 | | 7/2010 | Dausch et al. | |
| 2011/0237953 A1 | | 9/2011 | Olsson et al. | |
| 2013/0169818 A1 | | 7/2013 | Ko et al. | |

\* cited by examiner

*Primary Examiner* — Serkan Akar
*Assistant Examiner* — Vani Gupta
(74) *Attorney, Agent, or Firm* — Pai Patent & Trademark Law Firm; Chao-Chang David Pai

(57) ABSTRACT

An ultrasound probe structure dedicated for guiding the puncture needle. It has a passage in the center of the structure and the diameter of the passage is equal to the outer diameter of puncture needle. The bony and non-bony tissues can be distinguished according to the strength of the echoes so that the puncture needle can be guided to avoid hitting the bony tissue before or during insertion.

3 Claims, 7 Drawing Sheets

INVERTED BOWL SHAPED ULTRASOUND PROBE STRUCTURE OF GUIDING THE PUNCTURE NEEDLE

FIELD OF THE INVENTION

The present invention relates generally to an ultrasound probe with special structure, which is quite different from ordinary ones. Its operation frequency, radius of curvature, aperture diameter and special configuration of the piezoelectric transducer provide the insertion pathway of the needle, which is punctured into tissues, to be the same as the direction of the ultrasound guiding beam.

BACKGROUND OF THE INVENTION

Currently, the technique of tissue puncture for medical purpose is widely employed in clinics, such as anesthesia, analgesia, biopsy, aspiration, and etc. In a case, for example, during the procedure of epidural block in traditional way, it is not avoidable to hit the bony tissue under the blind fashion for needle puncture.

In recent years, the technique of needle puncture guided by ultrasound imaging for nerve block is frequently employed in clinics. Generally, a doctor operates the puncture needle with one or two hands and the other hand or a physician assistant operates the ultrasound probe to derive the image of tissues. It can be imagined that this kind of procedure is not ideal for two-man's or one-man's operation due to possible difficulty of coordination.

The recent ultrasound imaging systems for needle guidance in the market include GE LOGIQ e, Philips HD11 XE, SonoSite MicroMaxx, Zonare Medical Systems zone ultra, and etc. However, the ultrasound probes in those systems are unable to integrate with the puncture needle, or the ultrasound probe and the puncture needle are separate elements, so that the direction of ultrasound beam is not co-axial with the directions of the needle during puncture. In other words, the directions of ultrasound beam and the pathway of needle insertion will be not the same in these systems.

SUMMARY OF THE INVENTION

The objective of this invention is to provide an ultrasound probe with capability of integrating the puncture needle with co-axial feature, in the direction of ultrasound beam and the pathway of needle puncturing One feature of this invention is the integration of the ultrasound probe and the puncture needle. The geometric center of the ultrasound probe is designed with an adaptive passage corresponding to the outer diameter of the puncture needle for allowing the puncture needle to pass through.

Another feature of this invention is that either for A-mode or B-mode ultrasound probe is relatively easy to operate.

Another advantage of this invention is that the ultrasound probe includes at least two focal lengths, aperture diameters, and operation frequencies. The best focal length and the frequency may be designed according to the anatomical structure and the distribution of the puncture site close to the bone tissue.

To achieve the aims mentioned above, an ultrasound probe structure is provided and comprises an ultrasound probe, arranged a hollow passage in the center of the ultrasound probe; wherein the size of a focal zone and the operation frequency of each transducer are used to determine the range of a detecting area of the ultrasound probe.

So that the manner in which the above recited features of the present invention can be understand in detail, a more particular description of the invention, briefly summarized above, may be obtained by reference to embodiments, some of which are illustrated in the appended drawings. It is noted, however, that the appended drawings illustrate only typical embodiments of this invention and are therefore not to be considered limiting of its scope, for the invention may admit to other equally effective embodiments.

DETAILED DESCRIPTION OF THE INVENTION

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

The ultrasound probe in this invention may have at least one piezoelectric transducer, and the corresponding operations of the probe with four transducers, which demonstrate for A-mode only, are described in below as an example, respectively.

Figure 1A:
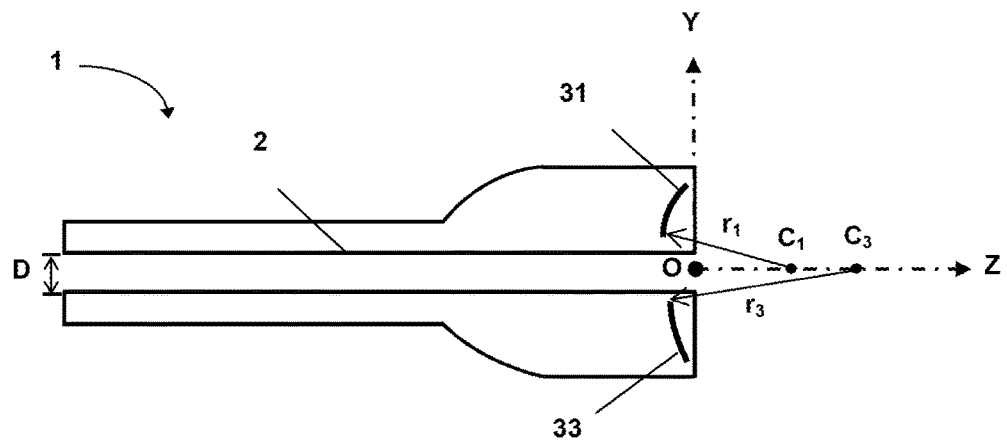
FIG. 1A is a sectional view showing a first embodiment of a center of a probe structure in YZ plan in accordance with this invention.
Figure 1B:
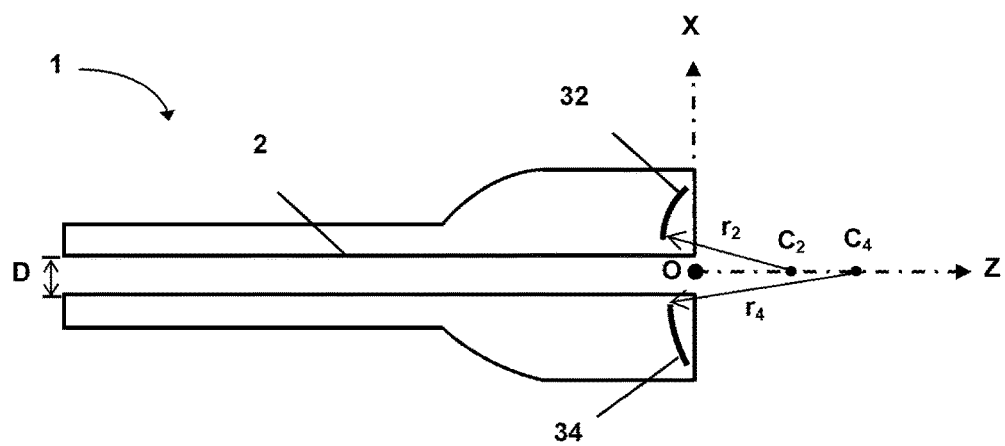
FIG. 1B is a sectional view showing the first embodiment of the center of the probe structure in XZ plan in accordance with this invention.
Figure 1C:
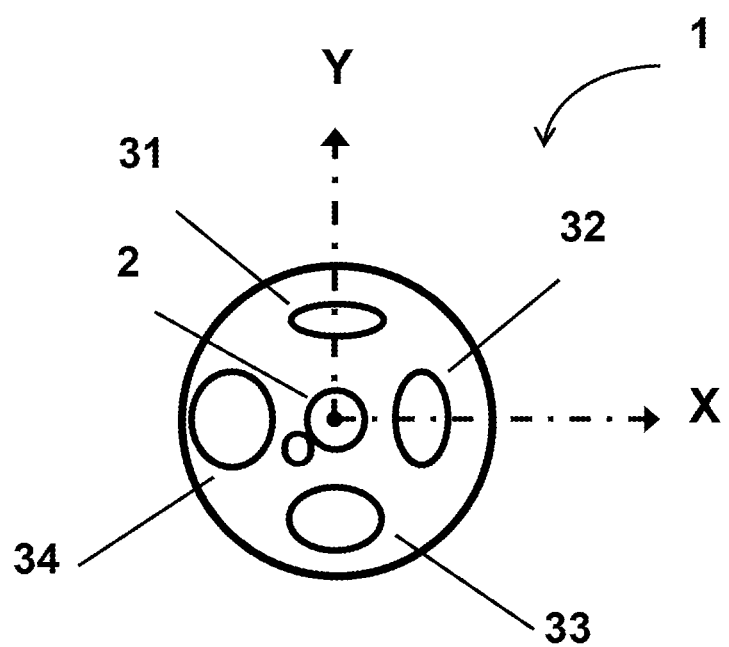
FIG. 1C is a sectional view showing the first embodiment of the center of the probe structure in XY plan in accordance with this invention.
Figure 2A:
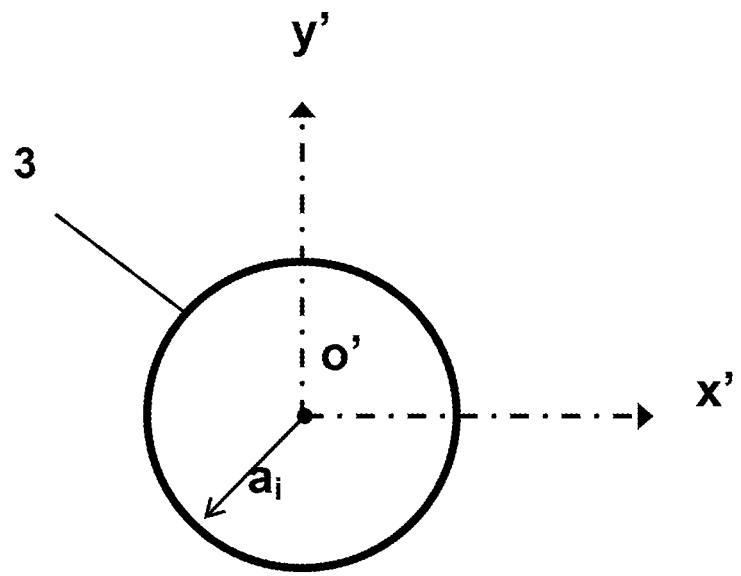
FIG. 2A is a sectional view showing a first embodiment of a piezoelectric transducer in X'Y' plan in accordance with this invention.

The center of the ultrasound probe 1 of this invention has a circular hollow passage 2, shown as FIGS. 1A and 2A. The size of the diameter D of the hollow passage 2 is designed according to the diameter of the puncture needle. The ultrasound probe 1 includes a plurality of piezoelectric transducers. This embodiment is described with four piezoelectric transducers, shown as FIG. 1C. Each piezoelectric transducer has a spherical bowl structure, and all piezoelectric transducers are arranged to surround the hollow passage 2. The arrangement is that the radii of the piezoelectric transducers are disposed with the same O-Z center line of the ultrasound probe 1, such as the first piezoelectric transducer 31, the second piezoelectric transducer 32, the third piezoelectric transducer 33, and the fourth piezoelectric transducer 34 with radii of curvature $r_1 \sim r_4$ respectively, shown as FIGS. 1A and 1B. Such arrangement may be confirmed that each piezoelectric transducer is capable of deriving the strongest echo signal on the path which the puncture needle goes forward. And the radii of the transducers curvatures and the aperture diameters of the transducers may be designed to make the ultrasound probe 1 to detect the A-mode signal from shallow to deep. The similar arrangement can also be applied to a linear array or phase array B-mode ultrasound probe. The radii of curvature r1~r4 of the first, second, third, and fourth piezoelectric transducers 31, 32, 33, 34 are $r_1 > r_2 > r_3 > r_4$. Therefore, the range of depth detected by the ultrasound probe 1 may be $C_1$-$C_4$ (FIGS. 1A and 1B).

Figure 2B:
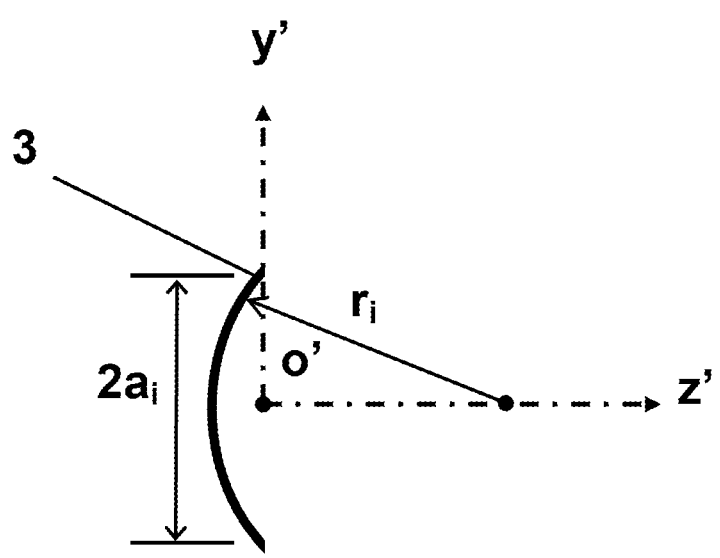
FIG. 2B is a sectional view showing a first embodiment of a piezoelectric transducer in Y'Z' plan in accordance with this invention.

Please refer to FIGS. 2A and 2B, the piezoelectric transducer 3 is further described. The detecting range along the O'-Z' line of the ultrasound probe 1 is determined by the width of the focal zone of each piezoelectric transducer 3. The aperture diameter of the piezoelectric transducer 3 is $2a_i$, the radius of curvature of the piezoelectric transducer 3 is $r_i$, and the f-number of the piezoelectric transducer 3 is defined as $r_i/2a_i$. The width of focal zone of the piezoelectric transducer 3 is proportional to the f-number thereof, thus the width of focal zone is adjusted by the f-number. However, the lateral resolution of the piezoelectric transducer 3 may be reduced while the width of the focal zone is increased. The lateral resolution may be increased by the relationship, that is, the operation frequency is inversely proportional to the focal length. Accordingly, the ultrasound probe 1 may be designed with several different piezoelectric transducers 3 to adjust the detecting range to achieve different aspects of clinical application.

Figure 3A:
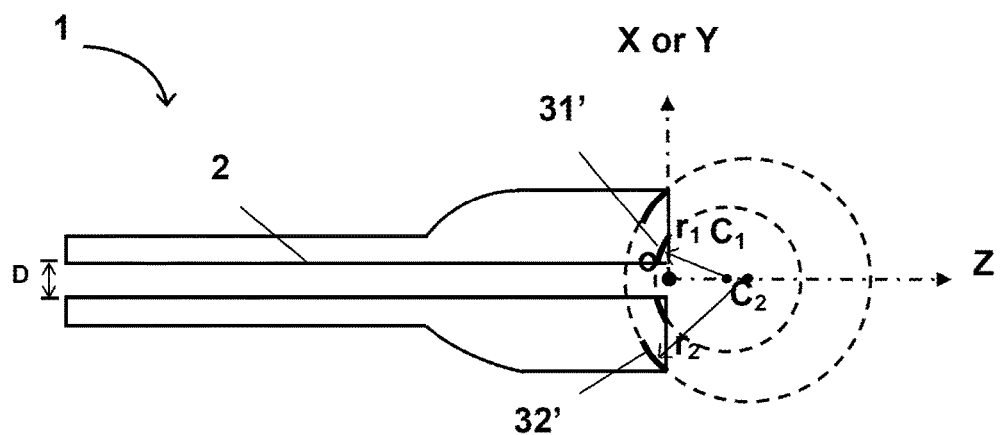
FIG. 3A is a sectional view showing a second embodiment of a center of a probe structure in XZ or YZ plan in accordance with this invention.
Figure 3B:
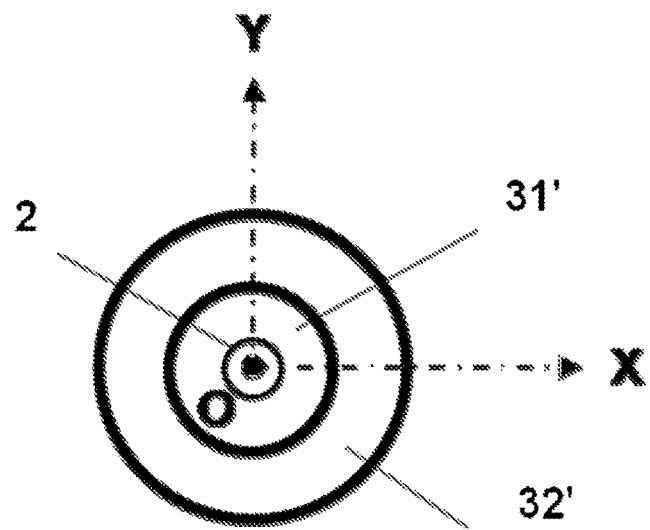
FIG. 3B is a sectional view showing the second embodiment of the center of the probe structure in XZ plan in accordance with this invention.
Figure 3C:
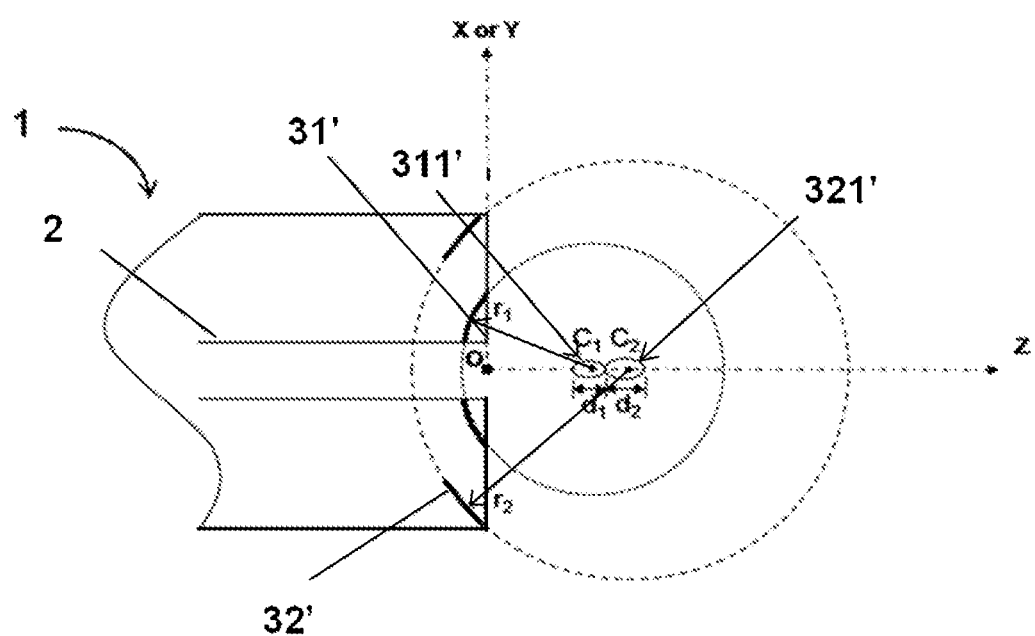
FIG. 3C is a sectional view showing a second embodiment of a piezoelectric transducer in XZ or YZ plan in accordance with this invention.

Another structure of the ultrasound probe and the arrangement of the piezoelectric transducer are shown as FIGS. 3A and 3B. The center of the ultrasound probe 1 of this invention is a circular hollow passage 2. The diameter D of the hollow passage 2 is designed according to the diameter of the puncture needle. The ultrasound probe 1 includes a plurality of piezoelectric transducer 3. This embodiment is described with two piezoelectric transducers 3. These two piezoelectric transducers 3 have curved ring structure, and the radii of curvature $C_1$ and $C_2$ are disposed with the same O-Z center line of the ultrasound probe 1, shown as the radii of curvature $r_1$ and $r_2$ of the first and second piezoelectric transducers 31' and 32' in FIG. 3A. Such arrangement may be confirmed that each piezoelectric transducer 3 is capable of deriving the strongest echo signal from tissues in the path which the puncture needle 4 goes forward. And the operation frequencies, the radii of curvature and the aperture diameters of the transducers may be designed to make the ultrasound probe 1 detect the A-mode signal from shallow to deep. Same idea is also applicable to the B-mode structure. The first and second focal zones 311', 321' shown as FIG. 3C are generated by the first and second piezoelectric transducers 31' and 32'. The focal lengths of the first and second focal zones 311', 321' are $d_1$ and $d_2$ respectively, and the depth range detected by the ultrasound probe 1 may be $d_1+d_2$.

Figure 4A:
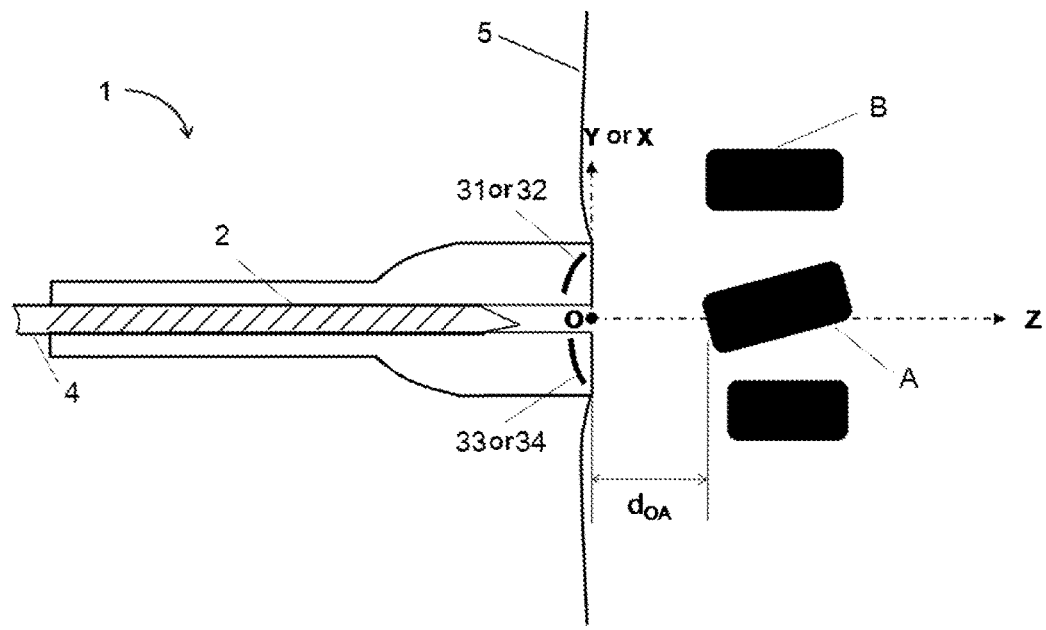
FIG. 4A is a schematic drawing showing the operation before puncturing in accordance with this invention.
Figure 4B:
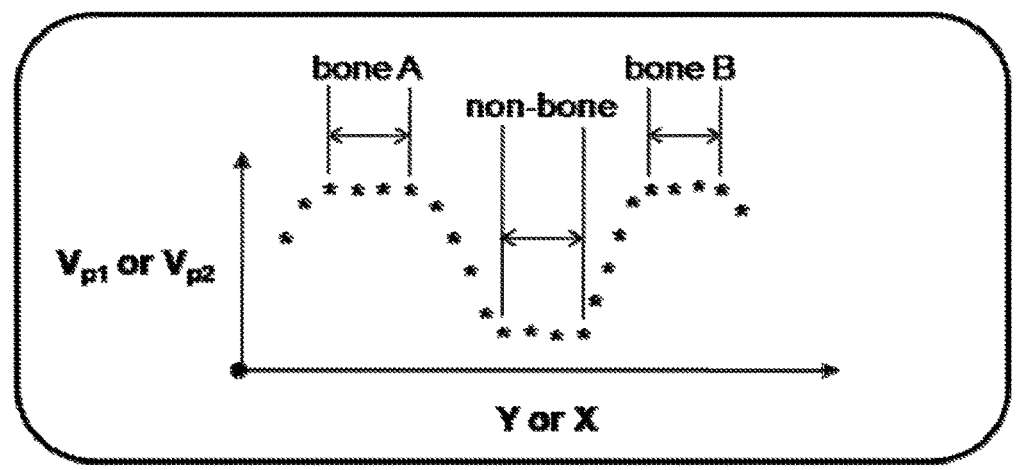
FIG. 4B is a schematic drawing showing the echo signal before puncturing in accordance with this invention.

The operation of this invention is shown as FIGS. 4A and 4B. Before the puncture needle 4 is inserted into skin 5, the doctor may operate the ultrasound probe 1 to move along Y or X direction, shown as FIG. 4A, and recognize the bone tissue by the strength of the echo signal from tissues. When the distance $d_{OA}$ between the bone tissue and the ultrasound probe 1 is within the range, which is able to detect the first piezoelectric transducer 31 or the second piezoelectric transducer 32, the relationship of the peak amplitude of the echo signal and the ultrasound probe 1 in the Y or X direction may be shown as FIG. 4B, that is, the VP1 and VP2 are referred to the peak amplitudes of echo signals detected by the first and second piezoelectric transducers 31 and 32, respectively.

In addition, when the O-Z center line of the ultrasound probe 1 passes through the bone tissue A as shown in FIG. 4B, the voltage value of the echo signal is relatively high and the doctor may move the ultrasound probe 1 to either Y or X direction. When the voltage value of the echo signal is relatively low, the doctor may continuously move the ultrasound probe 1 in the same direction till the voltage value of the echo signal becomes high again. Therefore, the doctor may be informed the range of low echo signal, and further the non-bone area in the Y or X direction is recognized. Once the non-bone area is confirmed the doctor starts to insert the needle.

Figure 5A:
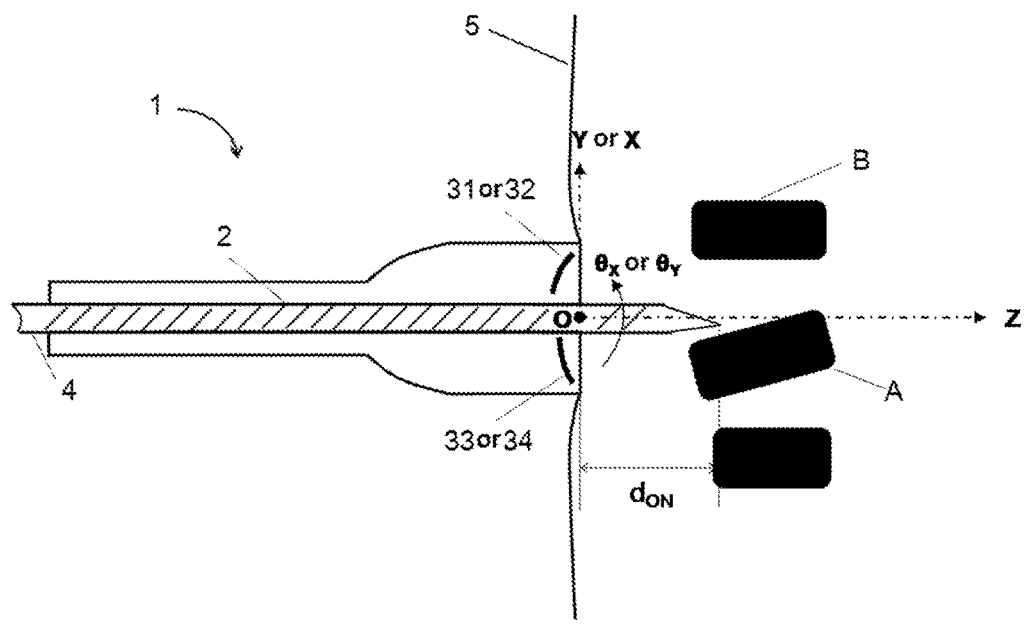
FIG. 5A is a schematic drawing showing the operation while puncturing in accordance with this invention.
Figure 5B:
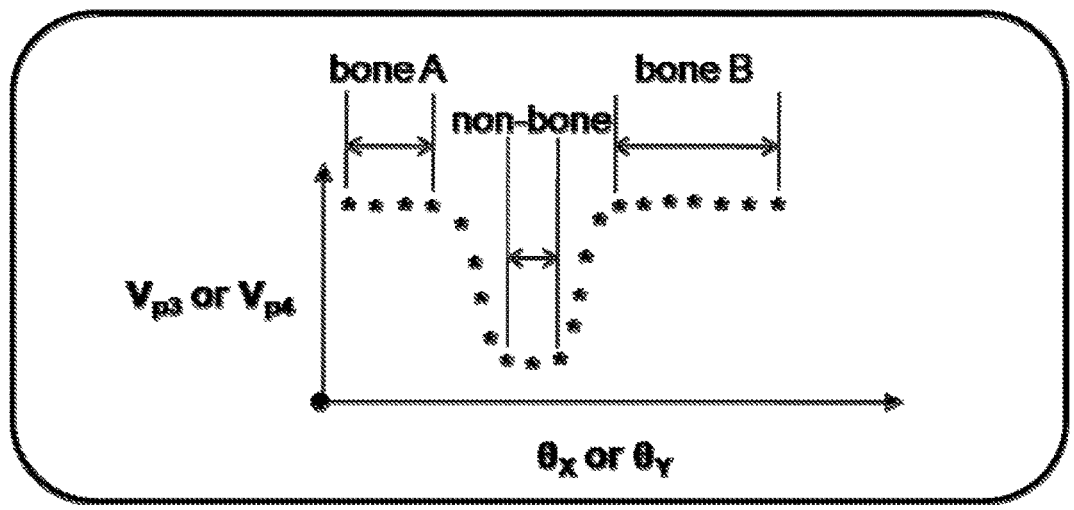
FIG. 5B is a schematic drawing showing the echo signal while puncturing in accordance with this invention.

When the puncture needle 4 is inserted in the body, the echo signal of the deep bone tissue may be detected by the third piezoelectric transducer 33 or by the fourth piezoelectric transducer 34 and the inserting depth $d_{ON}$ may be estimated by the scaling bars marked on the puncture needle 4. The doctor may confirm the echo signal of the third piezoelectric transducer 33 or the fourth piezoelectric transducer 34 with the value of $d_{ON}$. When the puncture needle 4 is encountered the condition which is shown as FIG. 5A, the peak amplitudes of echo signals $V_{P3}$ and $V_{P4}$ detected by the third piezoelectric transducer 33 or the fourth piezoelectric transducer 34 shall display relatively high values. When $\theta_X$ or $\theta_Y$ is zero degree, shown as FIG. 5B, $V_{P3}$ and $V_{P4}$ are relatively high. At this time, the doctor may rotate the ultrasound probe 1 along the Y or X axis. When $\theta_X$ or $\theta_Y$ is located in the some range, i.e. the O-Z center line of the ultrasound probe 1 does not pass through the bone tissue A and the bone tissue B, $V_{P3}$ and $V_{P4}$ shall have relatively low values. At this time, the doctor may continuously insert the needle until the target is reached. The configuration of various piezoelectric transducers in the ultrasound probe with coaxial feature of the ultrasound beam and the direction of needle insertion path can be realized by using the technique mentioned above.

The operation of the transducer, shown as FIGS. 3A and 3B, is similar to that mentioned above, that is, the depths of the bone tissue may be detected by the size of focal zones of different piezoelectric transducers.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. An ultrasound probe structure, comprising:

an ultrasound probe housing, configured to have a hollow passage in a center thereof, wherein the hollow passage is allocated disposed with a central line aligned along with a central line of the ultrasound probe housing and configured for a puncture needle configured to be placed inside and pass through coaxially;

a plurality of transducers, arranged within the ultrasound probe housing and surrounding the hollow passage, the plurality of transducers configured to have at least two different aperture diameters and operation frequencies, wherein each of the transducers is configured as a spherical inverted bowl shape, or an inverted curved ring shape, with a respective radius of curvature configured to have its center of curvature located at a respective point on the central line of the ultrasound probe housing, the plurality of transducers configured to have at least two different radii of curvature;

wherein the aperture diameter, the radius of curvature, and the operation frequency of each of the transducers are designed or adjusted wherein each of the transducers is configured to have a respective focal zone centered at the center of curvature and configured to have a focal length along the central line of the hollow passage and a focal width across the central line of the hollow passage;

wherein the focal zones of the plurality of transducers in combination form an overall detection range for the ultrasound probe structure, wherein the overall detection range is configured to be longer and covers a larger space than the focal zone of any of the transducers, and the puncture needle configured to be guided, by at least one of the transducers at any time as it passes through the hollow passage, for an overall depth corresponding to the overall detection range; and wherein the focal width of the focal zone of each of the transducers is adjusted by the f number and the operation frequency, wherein the f number is defined as $r_i/2a_i$, $r_i$ is the radius of curvature of the transducer, and $2a_i$ is the aperture diameter of the transducer.

2. The ultrasound probe structure as claimed in claim 1, wherein a diameter of the hollow passage is configured to have a diameter corresponding according to a diameter of the puncture needle.

3. The ultrasound probe structure as claimed in claim 1, wherein the lateral resolution of each of the transducers is improved by increasing the operation frequency of the transducer.

* * * * *